United States Patent [19]

Dobler et al.

[11] Patent Number: 4,987,229
[45] Date of Patent: Jan. 22, 1991

[54] PURIFICATION OF SALTS OF RIBOFLAVIN 5'-PHOSPHATE, IN PARTICULAR OF MONOSODIUM RIBOFLAVIN 5'-PHOSPHATE

[75] Inventors: Walter Dobler, Heidelberg; Manfred Eggersdorfer, Frankenthal; Joachim Paust, Neuhofen, all of Fed. Rep. of Germany

[73] Assignee: BASF Aktiengesellschaft, Ludwigshafen, Fed. Rep. of Germany

[21] Appl. No.: 323,795

[22] Filed: Mar. 15, 1989

[30] Foreign Application Priority Data

Mar. 31, 1988 [DE] Fed. Rep. of Germany ....... 3810957

[51] Int. Cl.$^5$ ................................................ C07F 9/08
[52] U.S. Cl. ..................................... 544/243; 544/244
[58] Field of Search ................................ 544/243, 244

[56] References Cited

U.S. PATENT DOCUMENTS 3,907,777  9/1975  Nagasawa et al. ................... 544/244
4,476,304 10/1984  Yokota et al. ....................... 544/244

FOREIGN PATENT DOCUMENTS 3230895  6/1983  Fed. Rep. of Germany .
2511686  2/1983  France .
0687556  9/1951  United Kingdom .

OTHER PUBLICATIONS

Chemical Abstracts, Band 89, No. 3, Jul. 17, 1978, Ref. No. 19426c; R. D. Johnson, "A Preparative Method for Purification of Purification of Riboflavin 5-Monophosphate"& Anal Biochem., 1978, 86(2).
Methods in Enzymology, Band 122, Seiten 209-220 (1986); P. Nielsen et al., "Preparation, Properties, and Sepatation by High-Performance Liquid Chromatography of Riboflavin Phosphates".
Methods in Enzymology, Band 122, Seiten 199-208 (1986); R. P. Hausinger et al., "Separation of Flavons and Flavin Analogs by High h-Performance Liquid Chromatography".
Methods in Enzymology, vol. 122 (1986), pp. 199-208. Separation of Flavins and Flavin Analogs by High-Performance Liquid Chromatography, Hausinger et al.
Methods in Enzymology, vol. 122 (1986), pp. 209-220. Preparation, Properties, and Separation by High-Performance Liquid Chromatography of Riboflavin Phosphates, Nielsen et al.
Chemical Engineering, Nov. 1954, p. 120.
Phosphorylation of Insoluble Riboflavin with Chlorophosphoric Acids Proves Key to Successful Large Scale Synthesis of a 33-Carbohydrates, vol. 83, 1975, Ref: 79551a, p. 695.
Riboflavin-5'-Monophosphate, Kumagai et al.
Chemical Abstracts, vol. 104, 1986, Ref: 19453n, p. 470. Purification of Riboflavin Monophosphates.
CA 89:19426c, "A Preparative Method for Purification of 5'-FMN", Johnson et al.
Fluka, p. 109, Catalog, 1989, Merk Index 190 381.

Primary Examiner—Mukund J. Shah
Assistant Examiner—Celia Chang
Attorney, Agent, or Firm—Oblon, Spivak, McClelland, Maier & Neustadt

[57] ABSTRACT

Salts of riboflavin 5'-phosphate which are obtained by phosphorylation of riboflavin and reaction of the resulting riboflavin 5'-phosphate (5'-FMN), contaminated with unconverted riboflavin and isomeric riboflavin monophosphates and diphosphates, with an alkali metal hydroxide or a nitrogen base are purified by a process in which (a) a roughly 1-15% strength by weight homogeneous, clear, aqueous 5'-FMN salt solution having a pH of from 4 to 7 is prepared from the crude 5'-FMN obtained in the phosphorylation, water and the alkali metal hydroxide or the nitrogen base, preferably sodium hydroxide solution, if necessary with heating at from 30° to 100° C., (b) the resulting solution is treated with a suitable polymeric adsorber resin and (c) the 5'-FMN salt substantially freed from unconverted riboflavin is isolated from the resulting solution and, if desired, the solution is fed to a subsequent fine purification.

Treatment with the suitable polymeric adsorber resin is advantageously carried out in a column filled with adsorber resin. The subsequent fine purification can be effected by evaporative crystallization or by chromatographing a 5'-FMN solution, containing from 1 to 15% by weight of dry substance, in water or in a mixture of water and a lower aliphatic alcohol, having a pH of from 4 to 7, in a minimum amount of from 5 to 50% of the bed volume of the column over RP silica gel derivatized with alkyl groups, using water, or a mixture of water and a lower aliphatic alcohol, as the eluant. Preparative chromatography of 5'-FMN salts over derivatized RP silica gel using water, or a mixture of water and a lower aliphatic alcohol, as the solvent and eluant is also claimed independently of pretreatment with the suitable adsorber resin.

15 Claims, No Drawings

PURIFICATION OF SALTS OF RIBOFLAVIN 5'-PHOSPHATE, IN PARTICULAR OF MONOSODIUM RIBOFLAVIN 5'-PHOSPHATE

The present invention relates to a process for the purification of salts of riboflavin 5'-phosphate (5'-flavin mononucleotide and therefore referred to as 5'-FMN below), in particular of the commercially available monosodium salt of 5'-FMN, the said salts being obtained in the phosphorylation of riboflavin and reaction of the resulting riboflavin 5'-phosphoric acid with aqueous bases.

5'-FMN is a compound which plays an important role as a coenzyme in various enzyme reactions in the living organism and which is therefore used in the form of its salts, in particular in the form of sodium 5'-FMN, as an additive in drugs, foods and animal feeds. Sodium 5'-FMN is also used as a starting material for flavin adenine dinucleotide, which is employed as a therapeutic agent against vitamin $B_2$ deficiency.

Industrially, sodium 5'-FMN is generally obtained by reacting riboflavin with a phosphorylating agent, such as partially hydrolyzed phosphoryl chloride, and then treating the resulting riboflavin 5'-phosphate with sodium hydroxide solution. Accordingly, it contains as impurities about 5–30% of unconverted riboflavin, isomeric riboflavin mononucleotides, such as 2'-FMN and 4'-FMN, and riboflavin dinucleotides (5',4'-FDN and 5',3'-FDN) and polyphosphates. Only 5'-FMN is a physiologically active form of the water-soluble riboflavin, i.e. the isomeric riboflavin monophosphates and polyphosphates have no vitamin $B_2$ activity. Products of interest are therefore those which contain a very high percentage of 5'-FMN. Furthermore, a high content of unconverted riboflavin is undesirable since this prevents the preparation of a stable, clear, homogeneous aqueous solution from the product. The commercial preparations generally generally do not contain more than 74% of sodium 5'-FMN, even when declared as highly pure sodium 5'-FMN A commercial product which contains not less than 70% of sodium 5'-FMN and not more than 5% of riboflavin and a highly pure commercial product which contains not less than 80% of sodium 5'-FMN, no unconverted riboflavin and, as by-products, only the isomeric monophosphates are desirable.

In all known processes for the preparation of monosodium 5'-FMN by phosphorylation of riboflavin, a crude product which still contains considerable amounts of unconverted riboflavin, as well as isomeric mono- and polyphosphates as byproducts, is initially obtained. In order to obtain a readily water-soluble product from which stable solutions can be prepared, it is essential substantially to reduce the riboflavin content. Otherwise, the solution becomes cloudy more or less rapidly, depending on the riboflavin content.

Chemical Engineering, November 1954, page 120 et seq., discloses that, in a production process, the 5'-FMN content is increased by bringing this product into aqueous solution with ethanolamine as the monosalt at room temperature and separating the 5'-FMN from the undissolved riboflavin by filtration. In the subsequent precipitation by means of ethanol, the 5'-FMN is obtained in concentrated form. However, the purification is incomplete, so that the process has to be repeated several times. Another disadvantage is that expensive filtration apparatuses are required for filtering off the undissolved riboflavin, since the riboflavin is obtained in the form of extremely fine crystals. Moreover, the ammonium salt formed in this procedure also has to be converted into the sodium salt in a further step. This process is therefore involved and expensive and entails high solvent consumption.

Furthermore, CA 83 (1975) 79551a discloses that sodium 5'-FMN can be purified by absorbing it on active carbon and thus separating it from riboflavin present in the eluate or from diphosphates. The sodium 5'-FMN is then desorbed with dilute NaOH and is obtained in the form of a very dilute solution. Since the desired product is absorbed in this process, large amounts of absorbers are required, with the result that this method is too expensive for an industrial process.

Furthermore, CA 104 (1986) 19453n discloses a purification process in which the isomeric monophosphates are absorbed on a defined anion exchanger and are eluted with a sodium chloride solution. The disadvantage of this process is that a very large volume of ion exchanger is required and, furthermore, the product fraction has to be separated from NaCl over another ion exchanger.

German Laid-Open Application DOS 3,230,895 furthermore discloses that 5'-FMN can be purified by chromatography over a weakly basic, modified ion exchanger. The eluant required in this procedure is a buffer having a pH of 3.8 and consisting of formic acid and NaCl. In this process too a further purification step is therefore required for removing the buffer after the separation.

A good overview of the current state-of-the-art in the purification of 5'-FMN is given in the reviews by P. Nielsen et al in Methods in Enzymology, 122 (1986), 209–220, and by R. Hausinger et al in ibid. 122 (1986), 199–208. In loc. cit. there is also a description of a preparative preparation of crude 5'-FMN over silica gel RP-18, in which elution is effected with an ammonium formate/formic acid buffer. Further purification methods described are the following:

(a) polysytrene-based ion exchanger with the use of buffer systems such as isopropanol/triethylammonium acetate, (b) cellulose-based ion exchanger with the use of buffer systems such as ammonium carbonate and (c) chromatography over immobilized flavokinase. However, this method is only suitable for very small amounts, owing to the expensive separation medium which has only a short life.

It is an object of the present invention to provide a process for the purification of salts of 5'-FMN, which makes it possible very substantially to remove the unconverted riboflavin from the phosphorylation mixture in a simple manner, without the disadvantages of the known processes, ie. as far as possible in only one purification step and with the use of only small amounts of purification assistants.

It is a further object of the invention to convert the salt of 5'-FMN, which has been substantially freed from riboflavin, into the desired products conforming to market products, in a very simple manner. This means the development of either a process for subsequent final chromatographic purification without the use of a salt solution or buffer solution as an eluant, or a suitable crystallization process.

We have found that these objects are achieved in that, surprisingly, the salts of 5'-FMN which are obtained in the phosphorylation of riboflavin and reaction of the resulting riboflavin 5'-phosphate (5'-FMN), contaminated with unconverted riboflavin and isomeric riboflavin monophosphates or diphosphates, with alkali metal hydroxides or nitrogen bases, in particular with sodium hydroxide solution, can be substantially freed from unconverted riboflavin if (a) a roughly 1-15, preferably roughly 4-6, % strength by weight homogeneous, clear aqueous crude 5'-FMN salt solution having a pH of from 4 to 8, preferably from 5.5 to 6.5, is prepared from the crude 5'-FMN obtained in the phosphorylation, water and the alkali metal hydroxide or the nitrogen base, in particular sodium hydroxide solution, if necessary with heating at 30-100° C., preferably 45-55° C., (b) the resulting solution is treated with a suitable polymeric adsorber resin in the form of small insoluble spheres which has particularly high mechanical strength, macroreticular porosity, a uniform pore size distribution, a large active surface area and a chemically homogeneous, nonionic structure and has been prepared by copolymerization from polystyrene/divinylbenzene, acrylic acid derivatives/divinylbenzene or methacrylic acid derivatives/divinylbenzene, and (c) the 5'-FMN salt substantially freed from unconverted riboflavin is isolated from the resulting solution or, if required, is converted into sodium 5'-FMN, and, if desired, the solution is then fed to a subsequent fine purification.

The process can be carried out particularly advantageously if the homogeneous aqueous crude 5'-FMN salt solution is passed through a column which is filled with the suitable polymeric adsorber resin, and the purified 5'-FMN salt is isolated from the resulting eluate, or the eluate is fed to a subsequent fine purification.

Polymeric adsorber resins which are suitable for the novel process are commercial polymers which have particularly high mechanical strength, macroreticular (sponge-like) porosity, a uniform pore size distribution, a large active surface area and a chemically homogeneous, nonionic structure, have been prepared by copolymerization from polystyrene/divinylbenzene (nonpolar), acrylic acid derivatives/divinylbenzene (polar) or methacrylic acid derivatives/divinylbenzene (moderately polar) and in general are commercially available in the form of small insoluble spheres.

The polar adsorber resins prepared by copolymerization of acrylic acid derivatives with divinylbenzene are particularly advantageously used, since regeneration is then simpler and no wetting problems are encountered with water. Examples of suitable adsorber resins are the Amberlites of the XAD series from Rohm & Haas, in particular Amberlite® XAD-1180 and Amberlite® XAD-7.

In general, not more than 20 g of riboflavin are adsorbed per liter of adsorber resin, whereas, at a suitable pH, the phosphorylated riboflavins are not bound.

The novel process is advantageously carried out by a method in which the crude 5'-FMN, which is obtained in the phosphorylation process and contains about 5-30% by weight of unconverted riboflavin, is suspended in water, the suspension is brought to a pH of from 4 to 8, preferably from 5.5 to 6.5, in particular about 6, with an alkali metal hydroxide or a nitrogen base, in particular with NaOH, and the crude 5'-FMN salt solution is prepared with gentle heating. The crude 5'-FMN can, if desired, be used directly in the form of the filter cake obtained in the phosphorylation and containing residual moisture.

Adjustment of the pH and hence formation of the 5'-FMN salt can in principle be effected with all alkali metal hydroxides or suitable nitrogen bases. Since to date there has been commercial demand only for the sodium salt, sodium hydroxide solution, which is also a particularly cheap reagent, is generally used. If bases other than NaOH are used, the purified 5'-FMN salt would, if desired, then have to be converted into sodium 5'-FMN.

Apart from NaOH, which is preferred, other alkali metal hydroxides are KOH and LiOH. Examples of nitrogen bases are $NH_4OH$, alkylamines, dialkylamines, trialkylamines, in which the alkyl groups are of 1 to 3 carbon atoms, and ethanolamines and cycloaliphatic amines, such as morpholine or piperidine.

The crude 5'-FMN salt solution obtained is then passed through the column filled with adsorber resin.

Depending on utilization of the adsorber resin capacity, the eluate contains from 0 to 5%, preferably from 0 to 1%, in particular only about 0.5%, of unconverted riboflavin and from 65 to 80% of 5'-FMN salt.

The adsorber resin is regenerated by washing with aqueous NaOH solution. The concentration of this NaOH solution should be 0.01-5, preferably about 0.1, molar. In this way, the riboflavin can be recovered in the form of a concentrated solution of its Na salt.

From the eluate obtained in the regeneration with aqueous NaOH solution, the riboflavin can be recovered in crystalline form by acidification, for example with a mineral acid, such as HCl or $H_2SO_4$, or a strong organic acid, such as oxalic acid or formic acid.

It was very surprising that separation of the riboflavin from the 5'-FMN solution having such a complex composition can be carried out in such a selective and well-defined manner by rapid passage of the solution through a suitable adsorber resin bed and the expensive multiple dissolution and precipitation sequences with complicated removal of the riboflavin, which is difficult to filter, according to the prior art can thus be dispensed with.

Other decisive advantages of the process are:
1. Because the riboflavin, which is present in a substantially smaller amount than the desired product, can be removed selectively by the adsorber resin, substantially smaller amounts of adsorber resin are required than in the known purification process, in which the desired product 5'-FMN is adsorbed.
2. The product solution is only slightly diluted as a result of passage through the adsorber resin (maximum dilution=2:1).
3. Only water may be used as the solvent, so that working up the solvent can be dispensed with.
4. Even after 50 cycles, there were no measurable changes in the adsorber material, so that the adsorber columns may be expected to have a very long life.
5. The unconverted riboflavin can readily be eluted in purified and concentrated form, so that a rapid adsorption/desorption sequence with little loss is possible.

We have furthermore found, surprisingly, that an aqueous solution of 5'-FMN salt substantially freed from riboflavin by treatment with the adsorber resin, preferably by passage through the adsorber resin column, can be further purified by preparative chromatography over a reversed phase silica gel derivatized with alkyl groups, even without the use of salt or buffer solutions foreign to the system, if a sufficient amount of an aqueous solution which is not too dilute is chromatographed. On the other hand, more highly dilute aqueous solutions cannot be separated in this manner.

The present invention therefore also relates to a process for the purification of 5'-FMN salt obtained by phosphorylation of riboflavin and reaction of the resulting riboflavin 5'-phosphate, contaminated with unconverted riboflavin, and isomeric riboflavin monophosphates and diphosphates, with an alkali metal hydroxide or a nitrogen base, preferably sodium hydroxide solution, wherein the 5'-FMN salt obtained as described above by treatment with the adsorber resin, preferably on passage through the adsorber resin column, and substantially freed from unconverted riboflavin and in the form of an aqueous solution containing from 1 to 15, preferably from 4 to 6, % by weight of dry substance and having a pH of from 4 to 8, preferably from 5.5 to 6.5, in particular about 6, is chromatographed in a minimum amount of from 5 to 50%, preferably from 8 to 20% of the bed volume (BV) of the column over a reversed phase (RP) silica gel derivatized with alkyl groups and having a particle size fraction of from 10 to 300 $\mu$m, preferably from 20 to 200 $\mu$m, using water, or a mixture of water and a lower aliphatic alcohol having an alcohol content of from 0 to 80%, as the eluant, under superatmospheric pressure.

The ratio of dry substance to separation material in this process step is from 1:200 to 1:7, preferably from 1:25 to 1:15, in particular about 1:20.

The separation material used is a commercial RP silica gel derivatized with alkyl groups and having the abovementioned particle size fraction. Known suitable commercial RP silica gels have particle size fractions of from 20 to 45 $\mu$m or from 30 to 70 $\mu$m. Examples are silica gel RP-8, silica gel RP-12 and silica gel RP-18, such as HD-SIL-RP-18 from Orpregen.

According to the invention, examples of lower aliphatic alcohols are methanol, ethanol, isopropanol and ethylene glycol. Methanol is particularly advantageously used.

Under the stated conditions, any riboflavin still obtained is adsorbed by the silica gel. If 5'-FMN solutions which have a riboflavin content of less than 1% are used for this fine purification, many successive separations can be carried out without the quality of the purification changing. When the chromatography process is complete, the adsorbed riboflavin can be eluted relatively simply by washing with a solvent containing more alcohol, for example with 60% strength aqueous methanol.

The actual chromatographic separation of 5'-FMN and its byproducts is carried out using water/alcohol mixtures which contain less alcohol, ie. from 1 to 20%, preferably about 10%, of alcohol.

For example, the use of silica gel HD-SIL-RP 18 (20–40 $\mu$m) and a 10:90 methanol/water mixture gives the following fractions:

1. a preliminary fraction containing polyphosphates, diphosphates and 3'-FMN,
2. an intermediate fraction containing from 70 to 85% of 5'-FMN in addition to 3'-FMN, 4'-FMN and 4',5'-FDN and
3. a main fraction containing >90% of 5'-FMN in addition to 4'-FMN and 2'-FMN. 97% strength 5'-FMN containing 3% of 2'-FMN is present in the second half of the elution peak.

Accordingly, up to 91% pure 5'-FMN can be obtained with the aid of this chromatographic fine purification step.

The water/alcohol mixture used as an eluant in the chromatography may be used in isocratic form, i.e. with a constant solvent ratio, or with a continuously changing solvent ratio (gradient elution). For example, very good separations can be achieved with eluants in which the methanol concentration increases from 0% to 30% in water.

It was surprising that no buffer solution is required for this preparative chromatographic separation. When all other conditions are adhered to but only analytical amounts of 5'-FMN solution are used, no separation is achieved. It is surprising that maintenance of a certain pH of the application solution results in the system being self-buffering if a sufficient amount of separating mixture is applied. This is the great advantage of the process, i.e. the fact that no buffer need be added. A buffer would be expensive and difficult to remove. It would have to be separated from the desired product in a further process step, and there would be a loss of the desired product and wastewater problems would occur. Another considerable advantage of the process is that it can be carried out using water or water containing a low percentage of alcohol as a solvent.

Of course, crude 5'-FMN salt solutions prepared by another method and substantially freed from unconverted riboflavin can also be purified in the manner described above. The present invention therefore also relates to a process for the preparative purification of monosodium riboflavin 5'-phosphate, substantially free of riboflavin and contaminated with isomeric flavin mononucleotides and flavin dinucleotides, by chromatographing a sodium 5'-FMN solution, under atmospheric or superatmospheric pressure, over an RP silica gel derivatized with alkyl groups and having a particle size fraction of from 10 to 300 $\mu$m, wherein a solution having a concentration of from 1 to 15, preferably from 4 to 6, % by weight of dry substance in water, or in a mixture of water and a lower aliphatic alcohol having an alcohol content of from 0 to 80% by weight, and a pH of from 4 to 7 is chromatographed in a minimum amount of from 5 to 50%, preferably from 8 to 20%, of the bed volume of the silica gel column, using water, or a mixture of water and a lower aliphatic alcohol having an alcohol content of from 0 to 80% by weight, as the eluant.

The present invention furthermore relates to a process for the purification of 5'-FMN salt obtained by phosphorylation of riboflavin and reaction of the resulting riboflavin 5'-phosphate, contaminated with unconverted riboflavin, and isomeric riboflavin monophosphates and diphosphates, with an alkali metal hydroxide or a nitrogen base, in particular sodium hydroxide solution, wherein the 5'-FMN salt obtained as described above by treatment with the suitable adsorber resin, substantially freed from unconverted riboflavin and in the form of an aqueous solution having a pH of from 4 to 8, preferably from 5.5 to 6, is evaporated down at from 20° to 100° C., preferably from 40° to 60° C., until the 5'-FMN salt crystallizes out, the suspension of crystals is cooled, preferably to about 20° C., the crystalline 5'-FMN salt is isolated and the mother liquor is recycled to the preparation process, if necessary after further evaporation and isolation of a second batch of crystals.

According to the prior art, sodium 5'-FMN can be precipitated from aqueous solution at a pH of from 5 to 6.5 also by the addition of ethanol. In this procedure, the diphosphates in particular remain in solution.

The novel crystallization has substantial advantages over the prior art.

1. Inorganic salts, such as NaCl or sodium phosphates, which originate from the phosphorylation process, always remain in solution, so that an on-spec product is always obtained.
2. 5'-FMN salt crystallizes out preferentially and 4'-FMN salt somewhat less preferentially, and, if still present, riboflavin crystallizes out, while 3'-FMN predominantly remains in the mother liquor and the diphosphates virtually completely remain in the mother liquor. Further 5'-FMN salt can be prepared from the mother liquors by partial hydrolysis and an acidcatalyzed rearrangement reaction.
3. Very good crystals are formed, ie. crystals which conform to product requirements and can be readily filtered off and washed can be prepared by suitable cooling.
4. The solvent used, water, is cheap and there are no working up problems.
5. As a result of possible recycling of the diphosphates and isomerization of the flavin mononucleotides, a maximum overall yield of 5'-FMN is obtained on the one hand and, on the other hand, there is less contamination of the wastewater with organic carbon.

It was surprising that no hydrolysis of the 5'-FMN salt or of the riboflavin occurs at the stipulated pH under these conditions of evaporative crystallization. Furthermore, it is surprising that, under these conditions, it is predominantly the concentration of 5'-FMN which increases and an on-spec product can be obtained by one crystallization stage.

With the aid of the novel process, the 5'-FMN obtained by phosphorylation of riboflavin can be substantially freed from unconverted riboflavin, isomeric flavin mononucleotides and flavin dinucleotides in a simple manner.

The Examples which follow illustrate the process.

EXAMPLE 1

(a) 2 l of a 5% strength solution obtained by phosphorylation of riboflavin, brought to a pH of 6 with NaOH and having the composition shown in Table I below,
(b) 2 l of water,
(c) 1 l of an aqueous 0.1 M NaOH solution and
(d) 2 l of water were pumped in succession through a column having a diameter of 9 cm and a bed volume (BV) of 2 l and filled with the adsorber resin XAD-7 from Rohm & Haas.

The eluate was monitored by means of a pH probe and a UV detector. The eluate was collected until the UV absorption had decreased to 10% of the maximum value. About 2 l of eluate having the composition shown in Table I below were obtained.

The eluate collected separately in the subsequent regeneration contained, in concentrated form, the riboflavin dissolved away from the ion exchanger by the NaOH solution. By monitoring the UV absorption, a very concentrated riboflavin solution was obtained. It was then acidified with HCl or with HCOOH and heated at the boil for 5 min, and the precipitate was filtered off, washed neutral with water and dried. About 85% of the absorbed riboflavin were recovered in this manner in the form of a roughly 98% pure product.

TABLE I

| | Crude 5'-FMN solution | | | Purified 5'-FMN solution | | |
|---|---|---|---|---|---|---|
| Solution | Riboflavin [%] | 5'-FMN [%] | Isomeric mono- and diphosphates [%] | Riboflavin [%] | 5'-FMN [%] | Isomeric mono- and diphosphates [%] |
| I | 20.8 | 64.5 | 14.4 | 0.6 | 80.3 | 19.1 |
| II | 18.9 | 57.9 | 23.9 | 0.5 | 76.0 | 23.5 |
| III | 14.5 | 60.1 | 25.4 | 0.0 | 74.3 | 25.7 |

EXAMPLE 2

The procedure was carried out as described in Example 1, except that, instead of the ion exchanger XAD-7, the ion exchanger XAD-1180 from the same company was used. The following result was obtained:

TABLE II

| | Crude 5'-FMN solution | | | Purified 5'-FMN solution | | |
|---|---|---|---|---|---|---|
| Solution | Riboflavin [%] | 5'-FMN [%] | Isomeric mono- and diphosphates [%] | Riboflavin [%] | 5'-FMN [%] | Isomeric mono- and diphosphates [%] |
| IV | 16.2 | 66.3 | 17.5 | 1.8 | 74.3 | 22.9 |

EXAMPLE 3

(Fine purification according to claim 8)

A chromatography column having an internal diameter of 30 cm was filled, over a length of 15 cm, with silica gel HD-SIL-RP 18 from Orpregen (20–45 μm) in 10:90 methanol/water. Thereafter, A. 1,000 ml (0.1 BV) and
B. 2,000 ml (0.2 BV)

of an aqueous 5'-FMN solution which had been treated with adsorber resin similarly to Example 1, had a concentration of 5% by weight of dry substance and had a pH of 6 were metered onto the column and were chromatographed with 10:90 methanol/water.

The eluate was investigated by measuring the UV absorption at 530 nm and was collected in three fractions in accordance with the elution diagram. The first fraction and the second fraction were each about ⅓ BV and the third fraction was about 2 BV. The 5'-FMN solution used and the fractions obtained were investigated by HPLC (Hypersil-ODS RP-18; 0.1 M ammonium formate/formic acid; pH=3.9; 24% of methanol, UV=435 nm). The compositions of the 5'-FMN solution used and of the 3 fractions obtained after metering in 0.1 BV (A) or 0.2 BV (B) of starting solution are shown in Table III below. The desired fractions (fractions II and III) were evaporated down at 60° C. in a rotary evaporator and cooled to 20° C. The product which crystallized out was filtered off under suction and washed with ice water.

TABLE III

| | Starting solution [% by wt.] | A. Metered amount 1,000 ml (10% of BV) | | | B. Metered amount 2,000 ml (20% of BV) | | |
|---|---|---|---|---|---|---|---|
| | | Fraction I (⅓ BV) [% by wt.] | Fraction II (⅓ BV) [% by wt.] | Fraction III (2 BV) [% by wt.] | Fraction I (⅓ BV) [% by wt.] | Fraction II (⅓ BV) [% by wt.] | Fraction III (2 BV) [% by wt.] |
| Ribovlavin | 0.5 | 0 | 0 | 0 | 0 | 0 | 0 |

TABLE III-continued

|  | A. Metered amount 1,000 ml (10% of BV) | | | B. Metered amount 2,000 ml (20% of BV) | | |
| --- | --- | --- | --- | --- | --- | --- |
|  | Starting solution [% by wt.] | Fraction I (⅓ BV) [% by wt.] | Fraction II (⅓ BV) [% by wt.] | Fraction III (2 BV) [% by wt.] | Fraction I (⅓ BV) [% by wt.] | Fraction II (⅓ BV) [% by wt.] | Fraction III (2 BV) [% by wt.] |
| 5'-FMN | 67.9 | 14.9 | 80.2 | 90.6 | 39.9 | 84.0 | 90.8 |
| 4'-FMN | 6.8 | 3.6 | 14.8 | 4.9 | 4.1 | 9.6 | 6.8 |
| 3'-FMN | 6.2 | 16.0 | 2.6 | 0.3 | 14.1 | 4.1 | 0.1 |
| 2'-FMN | 0.3 | — | 0.2 | 2.9 | — | — | 2.3 |
| Diphosphates | 18.3 | 65.5 | 2.25 | 1.9 | 41.9 | 2.1 | — |

EXAMPLE 4

(Fine purification according to claim 9)

A 5'-FMN solution obtained by phosphorylation of 70 g of riboflavin with $POCl_3 \cdot H_2O$ was brought to a pH of 5.5 and a concentration of 5% by weight with NaOH and passed through an adsorber resin bed (XAD-7) similarly to Example 1. This gave a 5'-FMN solution which was substantially free of unconverted riboflavin and whose composition is shown in Table IV. The solution thus obtained was evaporated down at about 50° C. This gave 200 g of a supersaturated solution, from which 5'-FMN crystallized out in high purity even at the elevated temperature. The suspension of crystals was cooled to about 20° C. and filtered, and the crystals were washed with a little ice water. The first batch of 62 g of crystals having the composition shown in Table IV was obtained.

By further evaporation of the filtrate to about 100 g at about 50° C. and cooling to about 20° C., a second batch of 20 g of crystals and the mother liquor having the composition shown in Table IV were obtained. The second batch of crystals obtained was recycled to the first crystallization, and the mother liquor was returned to the phosphorylation process.

TABLE IV

|  | Solution prior to crystallization | First batch of crystals | Second batch of crystals | Mother liquor |
| --- | --- | --- | --- | --- |
| Riboflavin | 0.8 | 0.7 | 0 | 0 |
| 5'-FMN | 71.8 | 78.8 | 31.4 | 19.0 |
| 4'-FMN | 10.9 | 11.4 | 11.5 | 5.3 |
| 3'-FMN | 8.2 | 5.7 | 21.6 | 16.2 |
| 2'-FMN | 0.4 | 0.2 | 0 | 0 |
| Diphosphates | 7.9 | 3.2 | 35.5 | 59.5 |

We claim:

1. A process for the purification of salts of riboflavin 5'-phosphate from a crude riboflavin 5'-phosphate solution which is obtained by phosphorylating riboflavin and reacting the resulting riboflavin 5'-phosphate, contaminated with unconverted riboflavin and isomeric riboflavin monophosphates and diphosphates, with an alkali metal hydroxide or a nitrogen base, to form said crude riboflavin 5'-phosphate solution, comprising the steps of:

forming an approximately 1–15 wt.% homogeneous clear aqueous riboflavin 5'-phosphate salt solution having a pH of from 4–8.

contacting said homogeneous clear aqueous riboflavin 5'-phosphate salt solution with a polymeric adsorber resin in the form of small insoluble spheres which have high mechanical strength, macroreticular porosity, a uniform pore size distribution, a large active surface area and a chemically homogeneous, nonionic structure and which have been prepared by copolymerization from polystyrene/divinylbenzene, acrylic acid derivatives/divinylbenzene or methacrylic acid derivatives/divinylbenzene to form a contacted solution containing the riboflavin 5'-phosphate salt, wherein unconverted riboflavin is adsorbed to the polymeric adsorber resin from said contacted solution, and isolating said contacted solution containing the riboflavin 5'-phosphate salt substantially free of riboflavin by removing the polymeric adsorber with the adsorbed free riboflavin.

2. The process of claim 1, wherein said alkali metal hydroxide is sodium hydroxide.

3. The process of claim 1, wherein said contacting step comprises passing said homogeneous clear aqueous riboflavin 5'-phosphate salt solution through a column filled with said polymeric adsorber.

4. The process of claim 1, wherein said polymeric adsorber is Amberlite® XAD-1180 or Amberlite® XAD-7.

5. The process of claim 1, wherein said homogeneous clear aqueous riboflavin 5'-phosphate salt solution has a pH of from 5.5–6.5.

6. The process of claim 1, further comprising regenerating said polymeric adsorber after said contacting step by washing said adsorber with a 0.01–5 molar aqueous sodium hydroxide solution.

7. The process of claim 6, further comprising acidifying said sodium hydroxide solution to obtain riboflavin in crystalline form.

8. The process of claim 1, further comprising heating said homogeneous clear aqueous riboflavin 5'-phosphate salt solution at 30°–100° C. during said forming step.

9. A process as claimed in claim 1, wherein the purified 5'-FMN salt is converted into sodium 5'-FMN.

10. The process of claim 1, further comprising fine purifying said contacted solution.

11. The process of claim 10, wherein said fine purification process is a preparative purification of monosodium riboflavin 5'-phosphate, wherein said monosodium riboflavin 5'-phosphate is substantially free of riboflavin and contaminated with isomeric flavin mononucleotides and flavin dinucleotides, comprising chromatographing on a reverse phase silica gel column a solution of from 1 to 15% by weight of said monosodium riboflavin 5'-phosphate in water where a mixture of water and a lower aliphatic alcohol having an alcohol content of from 0 to 80% by weight, in a minimum amount of from 5 to 50% of the bed volume of the silica gel column, and having a pH of from 4 to 8; wherein said reverse phase silica gel is derivatized with alkyl groups, and has a particle size fraction of from 10 to 300 μm; under atmospheric or super-atmospheric pressure, using water or a mixture of water and a lower aliphatic alcohol having an alcohol content of from 0 to 80% by weight, without added buffer, as the eluant.

12. The process of claim 11, wherein said reverse phase silica gel is silica gel RP-8, silica gel RP-12 or silica gel RP-18.

13. The process of claim 10, wherein said fine purifying step comprises evaporating said contacted solution at from 10°–100° C. until said riboflavin 5'-phosphate salt crystallizes to form a suspension, cooling the suspension of crystals to about 20° C., isolating the crystallized riboflavin 5'-phosphate to form a mother liquor, and recycling the mother liquor to said forming step.

14. The process of claim 13, further comprising the step of performing as second evaporation and a second isolation step on said mother liquor to obtain additional crystalline riboflavin 5'-phosphate prior to said recycling step.

15. The process of claim 11, wherein the solution being chromatographed contains 4 to 6% by weight of said monosodium 5'-phosphate.

* * * * *